United States Patent

Seidelmann et al.

[11] 4,219,551
[45] Aug. 26, 1980

[54] AMINOALKOXYPHENYLPYRROLIDONE ANTIHYPERTONIC AGENTS AND USE THEREOF

[75] Inventors: Dieter Seidelmann; Ralph Schmiechen; Gert Paschelke; Bernd Müller, all of Berlin, Fed. Rep. of Germany

[73] Assignee: Schering, Aktiengesellschaft, Berlin and Bergkamen, Fed. Rep. of Germany

[21] Appl. No.: 62,865

[22] Filed: Aug. 1, 1979

[30] Foreign Application Priority Data

Aug. 1, 1978 [DE] Fed. Rep. of Germany ....... 2834114

[51] Int. Cl.² .................. C07D 413/12; C07D 401/12; A61K 31/535; A61K 31/445
[52] U.S. Cl. .............................. 424/248.54; 424/246; 424/250; 424/267; 544/58.5; 544/141; 544/360; 544/372; 546/208
[58] Field of Search ...................... 544/141, 58.5, 360, 544/372; 546/208; 424/246, 248.54, 250, 267

[56] References Cited

U.S. PATENT DOCUMENTS

| | | | |
|---|---|---|---|
| 3,577,415 | 5/1971 | Cale | 544/141 |
| 4,120,969 | 10/1978 | Welstead | 546/208 |
| 4,139,620 | 2/1979 | Boswell et al. | 544/141 |

Primary Examiner—Henry R. Jiles
Assistant Examiner—R. W. Ramsuer
Attorney, Agent, or Firm—Millen & White

[57] ABSTRACT

Novel aminoalkoxyphenylpyrrolidones of the following formula show antihypertonic activity:

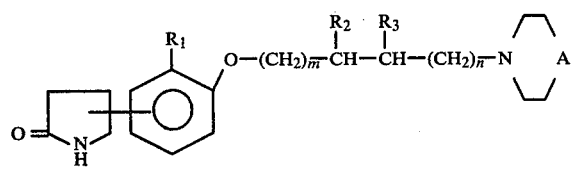

wherein
$R_1$ is H or $OCH_3$;
$R_2$ and $R_3$ are each, independently, H, $C_{1-4}$ alkyl, OH, $C_{1-6}$ acyloxy, or $C_{1-3}$ alkoxy;
m and n are each, independently, integers of from 0 to 3; and
A is $>O$, $>S$ $>N-R_5$, or $>CH-R_5$; $R_5$ is H,

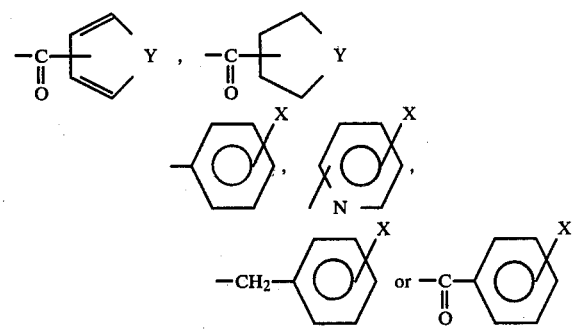

X is H, $C_{1-4}$ alkyl, $C_{1-4}$ alkoxy, halogen, $CF_3$, or $OCF_3$; and Y is O, S or NH;
and pharmaceutically acceptable salts thereof.

27 Claims, No Drawings

AMINOALKOXYPHENYLPYRROLIDONE ANTIHYPERTONIC AGENTS AND USE THEREOF

SUMMARY OF THE INVENTION

In a compositional aspect, this invention provides novel aminoalkoxyphenylpyrrolidones of Formula I

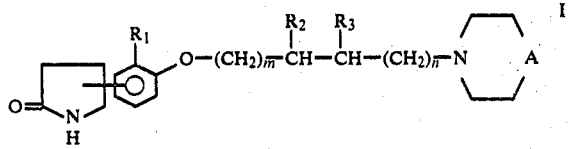

wherein
R$_1$ is H or OCH$_3$;
R$_2$ and R$_3$ are each, independently, H, C$_{1-4}$ alkyl, OH, C$_{1-6}$ acyloxy, or C$_{1-3}$ alkoxy;
m and n are each, independently, integers of from 0 to 3; and
A is >O, >S >N—R$_5$, or >CH—R$_5$; R$_5$ is H,

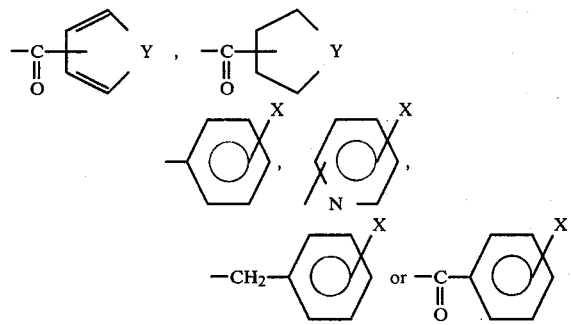

X is H, C$_{1-4}$ alkyl, C$_{1-4}$ alkoxy, halogen, CF$_3$, or OCF$_3$; and Y is O, S or NH;
and pharmaceutically acceptable salts thereof.

In a method of use aspect, this invention provides a method for treatment of cardiovascular diseases and hypertonia (high blood pressure) in mammals including humans, which comprises administering an amount of a compound of Formula I to a subject mammal effective for achieving the desired vasodilatory and/or antihypertonic (blood pressure lowering) effect or the desired treatment.

DETAILED DISCUSSION

The compounds of Formula I possess one or more asymmetric carbon atoms and can thus be prepared as racemates and/or optical antipodes. Both mixtures of enantiomers and diastereomers as well as pure enantiomers are within the scope of the invention, and within the meaning of Formula I.

The alkyl moiety of C$_{1-4}$ alkyl and C$_{1-4}$ alkoxy is understood to mean straight-or branched-chain lower alkyl residues, including methyl, ethyl, propyl, isopropyl, butyl, isobutyl, sec-butyl and tert-butyl. The alkyl group of C$_{1-3}$ alkoxy includes methyl, ethyl, propyl and isopropyl.

C$_{1-6}$ acyloxy is understood to mean acid residues of physiologically compatible acids of up to 6 carbon atoms. Preferred acids include formic acid, acetic acid, propionic acid, butyric acid, and caproic acid.

The moiety

is a residue of an unsubstituted amine, such as morpholine or thiomorpholine, or of an unsubstituted or 4-substituted piperazine or piperidine. Suitable such substituents include: phenyl and ortho-, meta- and para- substituted phenyl, such as o-tolyl, p-anisyl, p-fluorophenyl, m-trifluoromethylphenyl, and the like; 2-, 3- and 4-pyridyl, and pyridyl substituted at any remaining position, such as 6-methyl-2-pyridyl, 5-chloro-3-pyridyl, and the like; ortho-, meta- and para-substituted benzyl and benzoyl, such as o-xylyl and o-toluyl, p-methoxybenzyl and p-anisoyl, m-bromobenzyl and m-bromo-benzoyl, p-trifluoromethyoxybenzyl and p-trifluoromethoxybenzoyl, and the like; and saturated or aromatic heterocycles including 2- and 3-thenoyl, 2- and 3-tetrahydrothenoyl, 1-, 2- and 3-pyrrylcarbonyl, and 1-, 2- and 3-pyrrolidylcarbonyl, 2- and 3-tetrahydrofuroyl and 2- and 3-furoyl.

Preferred groups include:
4-phenylpiperazin-1-yl,
4- (3-chlorophenyl)-piperazin-1-yl,
4-(o-anisyl)-piperazin-1-yl,
4-(2-pyridyl)-piperazin-1-yl,
4(2-furoyl)-piperazin-1-yl,
4-(p-nitrophenyl)-piperazin-1-yl,
1-piperidyl, 4-phenyl-1-piperidyl,
4-(p-fluorobenzoyl)-1-piperidyl and morpholin-4-yl.

The 2-pyrrolidone ring may be substituted at C3, C4 or C5, although substitution at C4 is preferred.

The aminoalkoxy group is normally at C3 or C4 of the phenyl group, with the methoxy group at C4 or C3 when present.

The moiety linking the amino group and the phenolic oxygen, viz. —(CH$_2$)$_m$—CHR$_2$—CHR$_3$—(CH$_2$)$_n$, includes straight-or branched-chain alkyl groups as defined hereinbefore, which may be substituted with hydroxyl, acyloxy or alkoxy groups. Preferred moieties include 2-substituted (amine moiety) ethyl, 3-substituted propyl, 3-substituted 2-hydroxypropyl, 3-substituted 1-methylpropyl, 3-substituted 3-methylpropyl, 3-substituted 2-acetoxypropyl and 4-substituted butyl.

Salts of the compounds of Formula I may be made with any pharmaceutically acceptable mineral acid such as hydrochloric, hydrobromic, sulfuric, phosphoric and perchloric acid, and the like, with the hydrochloride being preferred. Salts may also be made with any pharmaceutically acceptable organic acid such as acetic, propionic, malic, tartaric, citric, benzoic and salicylic acid, and the like.

Illustrative compounds according to the invention include:
4-{4-Methoxy-3-[3-(4-phenylpiperazin-1-yl)-2-hydroxypropoxy]phenyl}-2-pyrrolidone, 4-{4-Methoxy-3-[3-(4-(3-chlorophenyl)-piperazin-1-yl)-2-hydroxypropoxy]phenyl }-2-pyrrolidone,
4-{4-Methoxy-3-[3-(4-(2-methoxyphenyl)piperazin-1-yl)-2-hydroxypropoxy]phenyl}-2-pyrrolidone,4-{4-Methoxy-3-[3-(4-(2-pyridyl)piperazin-1-yl)-2-hydroxypropoxy]phenyl}-2-pyrrolidone, 4-{4-Methoxy-3-[3-(4-(2-furoyl)piperazin-1-yl)-2-hydroxypropoxy]phenyl}-2-pyrrolidone, 4-{4-Methoxy-3-[3-(4-phenylpiperidin-1-yl)-2-hydroxypropoxy]phenyl}-2-pyrrolidone, 4-{4-Methoxy-3-[3-(4-morpholinyl)-2-hydroxypropoxy]phenyl}-2-pyrrolidone, 4-{4-Methoxy-3-[3-(4-(4-fluorobenzoyl) piperidin-1-yl)-2-hydroxypropoxy]phenyl}-2-pyrrolidone, 4-{3-Methoxy-4[3-(4-phenylpiperazin-1-yl)-2-hydroxypropoxy]phenyl}-2-pyrrolidone, 4-{3-[3-(4-Phenylpiperazin-1-yl)-2-hydroxypropoxy]-phenyl}-2-pyrrolidone, 5-{-4-Methoxy-3-[-3-(4-phenylpiperazin-1-yl)-2-hydroxypropoxy]-phenyl}- 2-pyrrolidone, 3-{4-Methoxy- 3-[3-(4-phenylpiperazin-1-yl)-hydroxypropoxy]phenyl}-2-pyrrolidone, 4-{4-Methoxy-3-[2-(4-phenylpiperazin-1yl)-ethoxy]phenyl}-2-pyrrolidone, 4-{4-Methoxy-3-(4-phenylpiperazin-1-yl)-propoxy]phenyl }-2-pyrrolidone, 4-{4-Methoxy-3-[3-(4-(4-fluorobenzoyl)piperidin-1-yl)propoxy]phenyl}-2- pyrrolidone, 4-{4-Methoxy-3-[4-(4-phenylpiperazin-1-yl)-butoxy]phenyl}-2-pyrrolidone, 4-{4-Methoxy-3-[3-(4-phenylpiperazin-1-yl)-2-acetoxypropoxy]phenyl}-2-pyrrolidone, 4-{4-Methoxy-3-[3-(4-piperazin- 1-yl)-1-methyl-2-hydroxy-propoxy]phenyl}-2-pyrrolidone, 4-{4-Methoxy-3-[3 -(4-phenylpiperazin- 1-yl)-2-hydroxypropoxy]phenyl}- 2-pyrrolidone dihydrochloride, 4-{4-Methoxy-3-[2-(4-phenylpiperazin-1-yl)-ethoxy]-phenyl}-2-pyrrolidone dihydrochloride, 4-{-4-Methoxy-3-[3-(4-(4-nitrophenyl)piperazin-1-yl)- 2-hydroxypropoxy]phenyl}-2-pyrrolidone, 4- {4-Methoxy-3-[3-methyl-3-(4-phenylpiperazin-1yl) propoxy]phenyl}-2-pyrrolidone, 4-{4-Methoxy-3[3-piperidino-2-hydroxypropoxy]phenyl}-2-pyrrolidone, and 4-{4-Methoxy-3-[3-methyl-3-(4-phenylpiperazin-1-yl)propoxy]-phenyl}-2-pyrrolidone dihydrochloride.

The compounds of Formula I may be prepared by fully conventional methods. For example, substituted phenyl-2-pyrrolidones of the Formula II

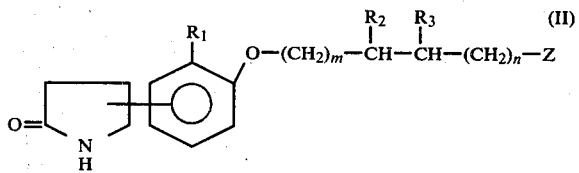

wherein $R_1$, $R_2$, $R_3$, m, and n are as defined for Formula I; and Z is (a) chlorine or (b) the oxygen atom of an epoxy group linked to the carbon atom in the β-position; may be condensed with a secondary cyclic amine of the Formula III

wherein A is as defined for Formula I; in a manner known per se, in an inert solvent, at temperatures above room temperature; optionally esterifying free hydroxy groups; and, if desired, converting the thus-obtained free amine of Formula I into the corresponding salt.

When the starting materials are compounds of Formula II(a) wherein Z is chlorine, the secondary amine of Formula III is advantageously utilized in a slight excess in the presence of an alkaline condensation agent in an inert solvent.

Suitable such inert solvents include: aliphatic and aromatic hydrocarbons, such as ligroin, hexane, benzene, and toluene; ethers, such as diethyl ether, glycol didimethyl ether, tetrahydrofuran, and dioxane; alcohols, such as methanol and isopropanol; halognated hydrocarbons, such as chloroform and methylene chloride; and polar aprotic solvents, such as dimethylformamide, dimethyl sulfoxide and hexamethylphosphoric triamide. These solvents can be used singly or as mixtures with one another.

Suitable alkaline condensation agents include: alkali and alkaline earth metal hydroxides, such as sodium hydroxide, potassium hydroxide and calcium hydroxide: alkali and alkaline earth metal carbonates, such as potassium carbonate and magnesium carbonate; alkali metal alcoholates, such as sodium methylate and potassium tert.-butylate; and tertiary amines, such as triethylamine and tributylamine.

The condensation reaction is generally effected at a temperature above room temperature, generally between 60° and 100° C. The reaction time ranges between one hour and eight hours.

When the starting materials are compounds of Formula II (b) wherein Z is the oxygen atom of an epoxy group linked to the carbon atom in the β-position, the secondary amine of Formula III is advantageously added in an equimolar amount, and the alkaline condensation agent may be omitted. It suffices to combine the two reactants in one or a mixture of the aforementioned inert solvents, for a comparable time and at a comparable temperature to the aforementioned condensation.

The starting compounds of the Formula II (b) may be obtained, insofar as they are unknown, by reacting the corresponding phenols with epichlorohydrin in the presence of an alkaline condensation agent.

The starting compounds of the Formula II (a), insofar as they are unknown, may be obtained from the aforementioned epoxides by reaction with hydrochloric acid. They can also be obtained directly by reacting the corresponding phenols with epichlorohydrin in the presence of catalytic amounts of a base, such as, for example, piperidine.

An alternative synthesis of compounds of the Formula I may be effected by reacting compounds of Formula II (c), wherein Z represents $NH_2$ (obtained by reacting the epoxides II (b) with ammonia) with a bishalogen alkyl compound of Formula IV

wherein A is as defined for Formula I; and hal is a halogen atom such as chlorine, bromine or iodine.

Esterification of a free hydroxy group may be effected according to conventional methods. A preferred procedure is reaction with a reactive acid derivative in the presence of an alkaline catalyst, such as, for example, reaction with an acid chloride or acid anhydride in the presence of pyridine.

Salt formation from the free amine likewise takes place according to known methods. For this purpose, the amine is precipitated with the desired acid from a dilute solution. Salts with hydrochloric acid are preferred, wherein the hydrochlorides are obtained.

In a method of use aspect, this invention relates to the use of the compounds of Formula I according to this invention as medicinal agents for the treatment of cardiovascular diseases and high blood pressure in mammals, including humans.

For therapeutic purposes, the compounds of Formula I according to this invention are advantageously administered orally in unit dosage form in a daily dosage of 0.1–500 mg., preferably 1–50 mg.

The forms of administrations to be applied orally contain the active agent in a quantity of about 0.05 to about 500 mg., preferably about 0.1 to about 25 mg. per dosage unit.

The compounds of Formula I may be in the form of tablets, granules, powder, capsules, and similar forms. The active agent is normally administered together with a pharmaceutically acceptable carrier or vehicle, such as, for example, lactose, magnesium stearate, kaolin, saccharose, corn starch, talc, stearic acid, gelatin, agar, pectin, and the like.

The compounds of this invention are unexpectedly superior in their efficacy as compared to conventional antihypertonic agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight. The melting points were determined on a Kofler hot stage.

The solvents utilized for recrystallization are indicated in parentheses following the melting points.

The compounds designated as crude products were tested for sufficient purity by thin-layer chromatography in at least two systems and with the aid of IR spectra.

All other compounds are analytically pure (C,H,N determination, IR, UV, and NMR spectra, thin-layer chromatography).

EXAMPLE 1

15.5 millimoles of 4-[3-(2,3-epoxypropoxy)-4-methoxyphenyl]-2-pyrrolidone is dissolved in 50 ml. of methanol. After the addition of 15.5 mmol of 1-phenylpiperazine (95% strength), the reaction mixture is heated for 3 hours under reflux. After cooling of the reaction solution, the solvent is removed under vacuum at 40°. The residue is taken up in 50 ml. of 1N hydrochloric acid and extracted twice with 100 ml. of chloroform. The aqueous phase is adjusted to be alkaline with 2N sodium hydroxide solution and thereafter extracted three times with ethyl acetate. The combined ethyl acetate phase are washed with saturated sodium chloride solution, and the solvent, after drying over sodium sulfate, is distilled off under vacuum. The residue is recrystallized from ethanol, thus obtaining in a 61% yield 4-{4-methoxy-3-[3-(4-phenylpiperazin-1-yl)-2-hydroxypropoxy ]phenyl}-2-pyrrolidone, m.p. 143°–144°.

The dihydrochloride is precipitated from ethereal hydrochloric acid, m.p. 167°–169°.

The 4-[3-(2,3-epoxypropoxy)-4-methoxyphenyl]-2-pyrrolidone (m.p. 124°–126°) needed as the starting compound is obtained by reacting 4-(3-hydroxy-4-methoxyphenyl)-2-pyrrolidone with epichlorohydrin and sodium hydride in dimethylformamide.

EXAMPLE 2

In accordance with the process set forth in Example 1, the compounds set forth in the table below are prepared from 4-[3(2,3-epoxypropoxy)-4-methoxyphenyl]-2-pyrrolidone and a secondary amine, wherein

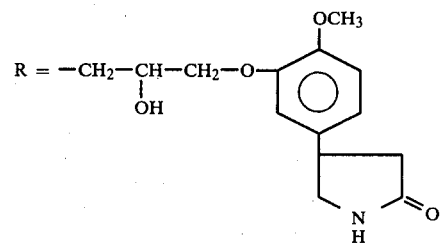

| Compound | Yield % | M.P. (°C.) | Recrystallized in | Temperature (°C.) | Time (h) | Solvent |
|---|---|---|---|---|---|---|
| 2a | 63 | 124–126 | Ethyl Acetate | 65 | 2 | Methanol |
| 2b | 54.5 | Oil | Chromatography MeOH/Chlf.: 2/8 | 65 | 2.5 | Methanol |
| 2c | 61 | 104–106 | Ethyl Acetate | 65 | 2 | Methanol |
| 2d | 33 | Oil | Chromatogr. CHCl₃:CH₃OH 9:1 | 83 | 4 | Isopropanol |

-continued

| Compound | Yield % | M.P. (°C.) | Recrystallized in | Temperature (°C.) | Time (h) | Solvent |
|---|---|---|---|---|---|---|
| 2e  R—N⟨piperidine⟩—phenyl | 64 | 146–147 | Ethyl Acetate | 65 | 1 | Methanol |
| 2f  R—N⟨piperidine⟩ | 20 | 107–108 | Acetone | 78 | 3 | Ethanol |
| 2g  R—N⟨morpholine⟩ | 83 | 92–94 | Ethyl Acetate | 65 | 1.5 | Methanol |
| 2h  R—N⟨piperidine⟩—C(=O)—C₆H₄—F | 47 | 160 | Methanol | 65 | 4 | Methanol |
| 2i  R—N⟨piperazine⟩—N—C₆H₄—NO₂ | 51 | 154–155 | Methanol | 65 | 3 | Methanol |

EXAMPLE 3

Analogously to the process according to Example 1, using 11.5 mmol of 4-[4-(2,3-epoxypropoxy)-3-methoxyphenyl]-2-pyrrolidone and 11.5 mmol of 1-phenylpiperazine (95% strength) as the starting compounds, 4-{3-methoxy-4-[3-(4-phenyl-piperazin-1-yl)-2-hydroxypropoxy]phenyl}-2-pyrrolidone in a 74% yield, m.p. 123°–125° (ethanol; after chromatography in methanol/chloroform 1:1).

The 4-[4-(2,3-epoxypropoxy)-3-methoxyphenyl]-2-pyrrolidone (m.p. 108°–110°) required as the starting material is obtained by reacting 4-(4-hydroxy-3-methoxyphenyl)-2-pyrrolidone with epichlorohydrin and sodium hydride in dimethylformamide.

EXAMPLE 4

From 8.6 mmol of 4-[3-(2,3-epoxypropoxy)phenyl]-2-pyrrolidone and 8.6 mmol of 1-phenylpiperazine (95% strength), 4-{3-[2-hydroxy-3-(4-phenylpiperazin-1-yl)propoxy]phenyl}-2-pyrrolidone, m.p. 82°–84°, is obtained analogously to Example 1 in a 77% yield (ether; after chromatography in methanol/chloroform 2:8).

The 4-[3-(2,3-epoxypropoxy)phenyl]-2-pyrrolidone (oil) needed as the starting compound is obtained by reacting 4-(3-hydroxyphenyl)-2-pyrrolidone with epichlorohydrin and sodium hydride in dimethylformamide.

EXAMPLE 5

From 10 mmol of 5-[3-(2,3-epoxypropoxy)-4-methoxyphenyl]-2-pyrrolidone and 10 mmol of 1-phenylpiperazine (95% strength), 5-{3-[2-hydroxy-3-(4-phenylpiperazin-1-yl)propoxy]-4-methoxyphenyl}-2-pyrrolidone, m.p. 127°–131° (ethanol) is obtained in 52% yield, analogously to the process of Example 1.

The 5-[3-(2,3-epoxypropoxy)-4-methoxyphenyl]-2-pyrrolidone (m.p. 140°–142°) required as the starting material is obtained by reacting 5-(3-hydroxy-4-methoxyphenyl)-2-pyrrolidone with epichlorohydrin and sodium hydride in dimethylformamide.

EXAMPLE 6

Using 10 mmol of 3-[3-(2,3-epoxypropoxy)-4-methoxyphenyl]-2-pyrrolidone and 10 mmol of 1-phenylpiperazine (95% strength), 3-{3-[2-hydroxy-3-(4-phenylpiperazin-1-yl)propoxy]-4-methoxyphenyl}-2-pyrrolidone, m.p. 146°–147°, is obtained in a 60% yield, analogously to the process of Example 1.

The 3-[3-(2,3-epoxypropoxy)-4-methoxyphenyl)]-2-pyrrolidone (m.p. 110°–112°) required as the starting material is obtained by reacting 3-(3-hydroxy-4-methoxyphenyl)-2-pyrrolidone with epichlorohydrin and sodium hydride in dimethylformamide.

EXAMPLE 7

20 mmol of 4-[3-(2-chloroethoxy)-4-methoxyphenyl]-2-pyrrolidone is dissolved in 50 ml. of dimethylformamide. After adding 22 mmol of 1-phenylpiperazine (95% strength) and 20 mmol of triethylamine, the reaction mixture is heated for 6 hours to 100 ° C. After the reaction has ceased, the solvent is withdrawn at 40° under a high vacuum. The residue is taken up in 50 ml. of ethyl acetate, washed with semisaturated sodium chloride solution, and the solvent, after drying over sodium sulfate, is distilled off under vacuum, thus obtaining in a 15.2% yield 4-{4-methoxy-3-[2-(4-phenylpiperazin-1-yl)ethoxy]-phenyl}-2-pyrrolidone, m.p. 140°–141°. The dihydrochloride, m.p. 219°–221°, is precipitated from ethereal hydrochloric acid.

The 4-[3-(2-chloroethoxy)-4-methoxyphenyl]-2-pyrrolidone (m.p. 134°–138°) needed as the starting material is obtained by reacting 1-bromo-2-chloroethane with 4-(3-hydroxy-4-methoxyphenyl)-2-pyrrolidone and sodium hydride in dimethylformamide.

EXAMPLE 8

According to Example 7, using 5 mmol of 4-[3-(3-chloropropoxy)-4-methoxyphenyl]-2-pyrrolidone and 5.5 mmol of 1-phenylpiperazine (95% strength), 4-{4-methoxy-3-[3-(4-phenylpiperazin-1-yl)propoxy]-phenyl}-2-pyrrolidone, m.p. 135°–137 ° (ethanol), is obtained in a 22.5% yield.

The 4-[3-(3-chloropropoxy)-4-methoxyphenyl]-2-pyrrolidone (m.p. 128°-130°) required as the starting compound is produced by reacting 4-(3-hydroxy-4-methoxyphenyl)-2-pyrrolidone with 1-bromo-3-chloropropane and sodium hydride in dimethylformamide.

EXAMPLE 9

Analogously to the process of Example 7, using 10 mmol of 4-[3-(3-chloropropoxy)-4-methoxyphenyl]-2-pyrrolidone and 11 mmol of 4-(4-fluorobenzoyl)piperidine, 4-{4-methoxy-3-[3-(4-fluorobenzoyl)piperidin-1-yl)propoxy]phenyl }-2-pyrrolidone is obtained in a 23% yield, m.p. 104°-105° (ethanol; after chromatography methanol/chloroform 9:1).

EXAMPLE 10

From 20 mmol of 4-[3-(4-bromobutoxy)-4-methoxyphenyl]-2-pyrrolidone and 22 mmol of 1-phenylpiperazine (95% strength), 4{4-methoxy-3-[4-(4-phenylpiperazin -1-yl)butoxy]phenyl}-2-pyrrolidone is obtained in a 30% yield, m.p. 123°-124° (ethyl acetate), analogously to the process of Example 7.

The 4-[3-(4-bromobutoxy)-4-methoxyphenyl]-2-pyrrolidone needed as the starting material (m.p. 116°-119°) is obtained by reacting 4-(3-hydroxy-4-methoxyphenyl)-2-pyrrolidone with 1,4-dibromobutane and sodium hydride in dimethylformamide.

EXAMPLE 11

7.5 mmol of 4-{4-methoxy- 3-[3-(4-phenylpiperazin-1-yl)-2-hydroxypropoxy]phenyl}-2-pyrrolidone is dissolved in 50 ml. of dry pyridine. After adding 15 mmol of acetic anhydride, the mixture is heated for 3 hours under reflux. After cooling, the reaction mixture is concentrated under vacuum. The residue is chromatographed over silica gel (acetone/dichloromethane 1:1) and recrystallized from isopropanol, thus obtaining in an 86% yield 4-{4-methoxy-3-[3-(4-phenylpiperazin-1-yl)-2-acetoxypropoxy]phenyl}-2-pyrrolidone, m.p. 128°-133°.

EXAMPLE 12

In accordance with the process set forth in Example 1, 10 mmol of 4-[3-(1-methyl-2,3-epoxypropoxy)-4-methoxyphenyl]-2-pyrrolidone and 10 mmol of 1-phenylpiperazine (95% strength) produce, in a 68% yield, 4-{4-methoxy-3-[3-(4-phenylpiperazin-1-yl)1-methyl-2-hydroxypropoxy]phenyl}-2-pyrrolidone, m.p. 116°-118° (ethanol).

The 4-[3-(1-methyl-2,3-epoxypropoxy)-4-methoxyphenyl]-2-pyrrolidone (m.p. 121°-125°) needed as the starting material is obtained by reacting 4-(3-hydroxy-4-methoxyphenyl)-2-pyrrolidone with 3-bromo-1,2-epoxybutane (prepared according to M. Santelli Tet.Let., 1977(50), 4397) and sodium hydride in dimethylformamide.

EXAMPLE 13

Analogously to Example 7, using 10 mmol of 4-[3-(3-bromobutoxy)-4-methoxyphenyl]-2-pyrrolidone and 11 mmol of 1-phenylpiperazine (95% strength), 4-{4-methoxy-3-[3-methyl-3-(4-phenylpiperazin-1-yl)propoxy]phenyl}-2-pyrrolidone is obtained in a 19.8% yield, m.p. 88°-90° (ethanol; after chromatography methanol/chloroform 1:9).

The dihydrochloride, m.p. 120° (decomposition ) is precipitated from ethereal hydrochloric acid.

The 4-[3-(3-bromobutoxy)-4-methoxyphenyl ]-2-pyrrolidone (oil) used as the starting material is obtained by reacting 1,3-dibromobutane with 4-(3-hydroxy-4-methoxyphenyl)-2-pyrrolidone and sodium hydride in dimethylformamide.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An aminoalkoxyphenylpyrrolidone of the formula

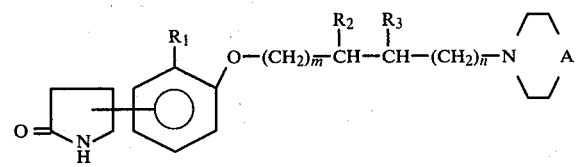

wherein $R_1$ is H or $OCH_3$;

$R_2$ and $R_3$ are each, independently, H, $C_{1-4}$ alkyl, OH, $C_{1-6}$ acyloxy, or $C_{1-3}$ alkoxy;

m and n are each, independently, integers of from 0 to 3; and

A is >O, >S >N—$R_5$, or >CH—$R_5$; $R_5$ is H,

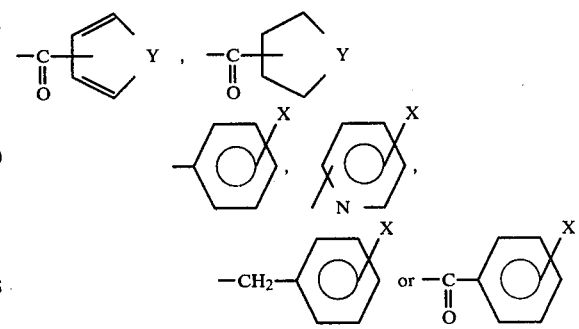

X is H, $C_{1-4}$ alkyl, $C_{1-4}$ alkoxy, halogen, $CF_3$, or $OCF_3$; and Y is O, S or NH;

and pharmaceutically acceptable salts thereof.

2. 4-{4-Methoxy-3-[3-(4-phenylpiperazin-1-yl)-2-hydroxypropoxy]phenyl}-2-pyrrolidone, a compound of claim 1.

3. 4-{4-Methoxy-3-[3-(4-(3-chlorophenyl)piperazin-1-yl)-2-hydroxypropoxy]phenyl}-2-pyrrolidone, a compound of claim 1.

4. 4-{4-Methoxy-3-[3-(4-(2-methoxyphenyl)piperazin -1-yl)-2-hydroxypropoxy]phenyl}-2-pyrrolidone, a compound of claim 1.

5. 4-{4-Methoxy -3-[3-(4-(2- pyridyl)piperazin-1-yl)-2-hydroxypropoxy]phenyl}-2-pyrrolidone, a compound of claim 1.

6. 4-{4-Methoxy-3-[3-(4-(2-furoyl)piperazin-1-yl)-2-hydoxypropoxy]phenyl}-2-pyrrolidone, a compound of claim 1.

7. 4-{4-Methoxy-3-[3-(4-phenylpiperidin-1-yl)-2-hydroxypropoxy]phenyl}-2-pyrrolidone, a compound of claim 1.

8. 4-{4-Methoxy-3-[3-morpholino-2-hydroxypropoxy]phenyl}-2-pyrrolidone, a compound of claim 1.

9. 4-{4-Methoxy-3-[3-(4-(4-fluorobenzoyl)piperidin-1-yl)-2-hydroxypropoxy]phenyl}-2-pyrrolidone, a compound of claim 1.

10. 4-{3-Methoxy-4-[3-(4-phenylpiperazin-1-yl)-2-hydroxypropoxy]phenyl }-2-pyrrolidone, a compound of claim 1.

11. 4-{3-[3-(4-Phenylpiperazin-1yl)-2-hydroxypropoxy]phenyl}-2-pyrrolidone, a compound of claim 1.

12. 5-{4-Methoxy-3-[3-(4-phenylpiperazin-1-yl)-2-hydroxypropoxy]phenyl}-2-pyrrolidone, a compound of claim 1.

13. 3-{4-Methoxy-3-[3-(4-phenylpiperazin-1-yl)-2-hydroxypropoxy]phenyl }-2-pyrrolidone, a compound of claim 1.

14. 4-{4-Methoxy-3-[2-(4-phenylpiperazin-1-yl)-ethoxy]phenyl}-2-pyrrolidone, a compound of claim 1.

15. 4-{4-Methoxy-3-[3-(4-phenylpiperazin-1-yl) -propoxy]phenyl }-2-pyrrolidone, a compound of claim 1.

16. 4-{4-Methoxy- 3-[3-(4-(4-fluorobenzoyl)piperidin-1-yl)propoxy]phenyl}-2-pyrrolidone, a compound of claim 1.

17. 4-{4-Methoxy- 3-[4-(4-phenylpiperazin -1-yl)-butoxy]phenyl}-2-pyrrolidone, a compound of claim 1.

18. 4-{4-Methoxy-3-[3-(4-phenylpiperazin-1-yl)-2-acetoxypropoxy]phenyl}-2-pyrrolidone, a compound of claim 1.

19. 4-{4-Methoxy -3-[3-(4 -piperazin-1-yl) -1-methyl-2-hydroxypropoxy]phenyl}-2-pyrrolidone, a compound of claim 1.

20. 4-{4-Methoxy-3-[3-(4-phenylpiperazin-1-yl)-2-hydroxypropoxy]phenyl }-2-pyrrolidone dihydrochloride, a compound of claim 1.

21. 4-{4-Methoxy -3-[2-(4-phenylpiperazin-1-yl)-ethoxy]phenyl}-2-pyrrolidone dihydrochloride, a compound of claim 1.

22. 4-{4-Methoxy-3-[3-(4-(4-nitrophenyl) piperazin-1-yl)-2-hydroxypropoxy]phenyl}-2-pyrrolidone, a compound of claim 1.

23. 4-{4-Methoxy-3-[3-methyl -3-(4-phenylpiperazin-1-yl)propoxy]phenyl}-2-pyrrolidone, a compound of claim 1.

24. 4-{4-Methoxy-3[3-piperidino-2-hydroxypropoxy]phenyl}-2-pyrrolidone, a compound of claim 1.

25. 4-{4-Methoxy-3-[3-methyl-3-(4-phenylpiperazin-1-yl)propoxy]phenyl}-2-pyrrolidone dihydrochloride, a compound of claim 1.

26. A pharmaceutical composition which comprises an effective antihypertonic amount of a compound of claim 1, and a pharmaceutically acceptable carrier.

27. A method of treating hypertonia in mammals which comprises administering an effective antihypertonic amount of a composition of claim 26.

* * * * *